United States Patent
Rezach et al.

(10) Patent No.: US 10,188,427 B2
(45) Date of Patent: Jan. 29, 2019

(54) SPINAL CONSTRUCT AND METHOD

(71) Applicant: WARSAW ORTHOPEDIC, INC., Warsaw, IN (US)

(72) Inventors: William Alan Rezach, Atoka, TN (US); Jason M. May, Cordova, TN (US)

(73) Assignee: Warsaw Orthopeic, Inc., Warsaw, IN (US)

( * ) Notice: Subject to any disclaimer, the term of this patent is extended or adjusted under 35 U.S.C. 154(b) by 0 days.

(21) Appl. No.: 15/499,447

(22) Filed: Apr. 27, 2017

(65) Prior Publication Data
US 2017/0224385 A1   Aug. 10, 2017

Related U.S. Application Data

(62) Division of application No. 14/645,179, filed on Mar. 11, 2015.

(60) Provisional application No. 61/951,382, filed on Mar. 11, 2014.

(51) Int. Cl.
*A61B 17/70* (2006.01)

(52) U.S. Cl.
CPC ...... *A61B 17/7014* (2013.01); *A61B 17/7007* (2013.01); *A61B 17/7025* (2013.01)

(58) Field of Classification Search
CPC ........... A61B 17/7035–17/704; A61B 17/7007
USPC ................................................. 606/250–253
See application file for complete search history.

(56) References Cited

U.S. PATENT DOCUMENTS

| | | | | |
|---|---|---|---|---|
| 6,022,350 A * | 2/2000 | Ganem | ............... | A61B 17/7059 606/272 |
| 2003/0093078 A1* | 5/2003 | Ritland | ............. | A61B 17/7007 606/900 |
| 2007/0135817 A1* | 6/2007 | Ensign | ............... | A61B 17/7007 606/96 |
| 2008/0071273 A1* | 3/2008 | Hawkes | ............. | A61B 17/7007 606/279 |
| 2008/0140075 A1* | 6/2008 | Ensign | ............... | A61B 17/7007 606/60 |
| 2008/0234743 A1* | 9/2008 | Marik | .................. | A61B 17/705 606/257 |
| 2010/0094345 A1* | 4/2010 | Saidha | ............... | A61B 17/7049 606/250 |
| 2014/0236239 A1* | 8/2014 | Biedermann | ...... | A61B 17/7037 606/278 |

* cited by examiner

*Primary Examiner* — Nicholas J Plionis

(57) ABSTRACT

A spinal construct is provided including a first fastener, a second fastener and a connector. Each fastener includes a first end and a second end configured for penetrating tissue. The connector has two ends. Each end of the connector includes an expandable member. The first end of each fastener is engageable to an expandable member of the connector to fix the fastener to the connector. The first and second ends of the connector are connected by a bridge. The spinal construct also includes securing members for attaching the connector to the fasteners. A method for treating a spinal disorder with the spinal construct is also provided.

20 Claims, 3 Drawing Sheets

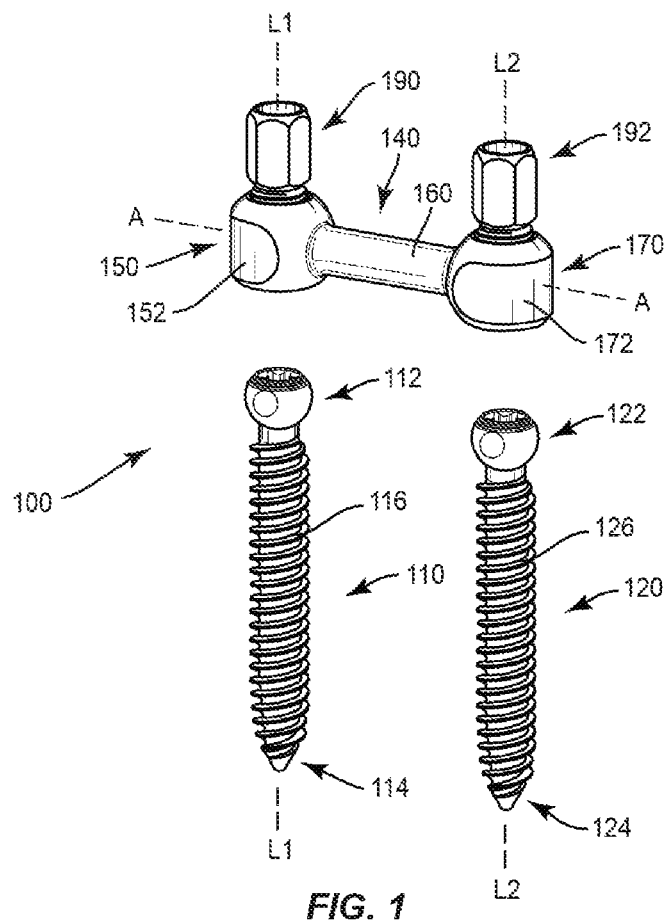
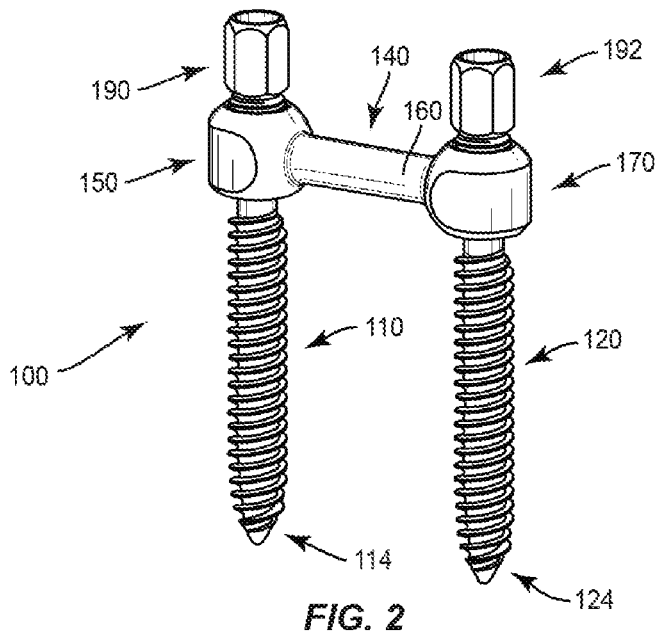

SPINAL CONSTRUCT AND METHOD

CROSS-REFERENCE TO RELATED APPLICATIONS

This application is a divisional of application U.S. patent application Ser. No. 14/645,179, filed on Mar. 11, 2015, which claims priority to U.S. Patent Application No. 61/951,382, filed Mar. 11, 2014. These applications are hereby incorporated by reference herein, in their entireties.

TECHNICAL FIELD

The present disclosure generally relates to medical devices for the treatment of musculoskeletal disorders, and more particularly to a surgical system and method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs, which include implants such as bone fasteners, connectors, plates and vertebral rods, are often used to provide stability to a treated region. These implants can redirect stresses away from a damaged or defective region while healing takes place to restore proper alignment and generally support the vertebral members. Surgical instruments are employed, for example, to engage the fasteners for attachment to the exterior of two or more vertebral members. This disclosure describes an improvement over these prior art technologies.

SUMMARY

In one embodiment, a spinal construct is provided including a first fastener, a second fastener and a connector. Each fastener includes a first end and a second end configured for penetrating tissue. The connector has a first end including a first expandable member and a second end including a second expandable member. The first end of each fastener can engage with the expandable members of the connector to fix the fasteners to the connector. The first end and the second end of the connector are joined by a bridge.

In another embodiment, a spinal construct is provided including a first fastener, a second fastener, a connector and securing members for attaching the connector to the first and second fastener.

In other embodiments, a method for treating a spinal disorder is provided. The method includes implanting a spinal construct comprising a first fastener, a second fastener and a connector. The connector utilized in this method has two ends, a first end including and first expandable member and a second end including a second expandable member. After the spinal construct is implanted, the method includes securing the first end of the connector to the first fastener with a first securing member and securing the second end of the connector to the second fastener with a second securing member. In various embodiments, the method provided herein is for treating a spinal disorder, wherein the spinal construct conforms to the curvature of the spine.

BRIEF DESCRIPTION OF THE DRAWINGS

The present disclosure will become more readily apparent from the specific description accompanied by the following drawings, in which:

FIG. 1 is a perspective view of components of one embodiment of a surgical implant system in accordance with the principles of the present disclosure;

FIG. 2 is a perspective view of the components shown in FIG. 1;

DETAILED DESCRIPTION

Figure 3:
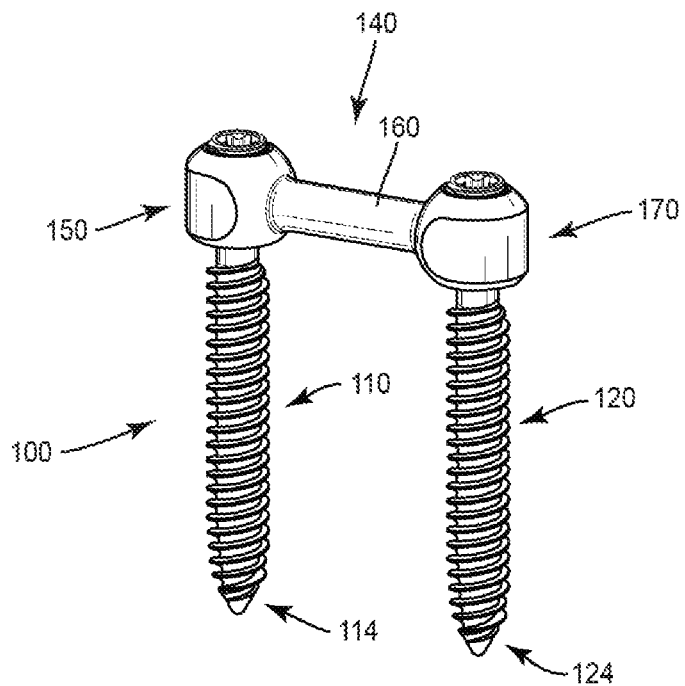
FIG. 3 is a perspective view of the components shown in FIG. 1.

The exemplary embodiments of a surgical system are discussed in terms of medical devices for the treatment of musculoskeletal disorders and more particularly, in terms of a surgical implant system and a method for treating a spine. In some embodiments, the system comprises a spinal construct and related methods of use, which include a pop on, snap on, click on and/or slide on member that provides a universal connection system to spine surgeons. In some embodiments, the spinal construct allows the use of a singular bone screw component with multiple types of receivers minimizing inventor while creating assemblies customized for a specific patient.

In one embodiment, the present system comprises a low profile pedicle screw construct. In some embodiments, the present system comprises a spinal construct having a single level construct that is aligned with the bone screws, which do not include an implant receiver or head. The single level spinal construct as described herein allows an intervertebral rod or connector to be disposed in-plane or in-line with the top of a bone screw or fastener instead of having a spinal rod lay on top of the bone screw sphere. The construct includes at least one pop on, snap on, click on and/or slide on member that is engaged with a top of the bone screws or fasteners for fixation and/or locking therewith. In some embodiments, the screws include heads, such as, for example, spheres such that this configuration allows a spinal rod of the construct to be in-plane or in-line with the screw spheres.

In one embodiment, the present system comprises a single vertebral level pop on construct. In this embodiment, the construct includes a first end having a pop on member, such as, for example, a receiver. The pop on member, in some embodiments, includes an expandable member, for example an expansion chamber configured for disposal of a retaining member or crown and a ring. The ring is expandable to facilitate receiving a sphere of a bone screw within the chamber and then retracts or contracts to fix the sphere within the first end of the connector of the construct. The sphere is seated with the crown in the expansion chamber in a retained configuration. A set screw is threaded with the first end and engageable with crown to lock the screw with the construct. In some embodiments, the construct includes a connector having a first end having a pop on member and a second end having a pop on member, as described herein. In some embodiments, the construct includes securing members, for example set screws, for engagement with the first end and the second end, as described herein.

In one embodiment, the construct is employed with a method such that bone screws are positioned with surgical site adjacent vertebrae. The construct is aligned with the bone screws or fasteners, which can be implanted into one level of the spine. In some embodiments, the construct comprises a single vertebral level construct and includes a first end that is snapped onto a first bone screw and a second end that is snapped onto a second bone screw. The construct includes set screws that are fixed with the end of the construct to tighten the screws with the construct. In one embodiment, the construct has a low profile configuration comprising a 4-5 millimeter profile compared with multi-axial pedicle screws.

In one embodiment, the construct comprises an adjustable element for a multi-span single vertebral level construct, which includes a first member that is translatable relative to a second member. In one embodiment, the second member is axially translatable relative to the first member and is slidable along a longitudinal axis of the construct. In one embodiment, the second member is rotatable relative to the first member about the longitudinal axis. In one embodiment, the second member is selectively axially translatable relative to the first member and the construct includes a set screw that fixes relative position of the members, as described herein. In one embodiment, the second member is engageable with the first member to selectively prevent rotation of the second member relative to the first member. In one embodiment, the first member and/or the second member includes a receiver having at least one pop on, snap on, click on and/or slide on member that is engaged with screws for fixation and/or locking therewith. In one embodiment, at least one of the members includes a C shaped receiver that allows a spinal rod to be inserted from a medial and/or lateral direction.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-6, there are illustrated components of a surgical implant system comprising a spinal construct 100, in accordance with the principles of the present disclosure.

The components of spinal construct 100 can be fabricated from biologically acceptable materials suitable for medical applications, including metals, synthetic polymers, ceramics and bone material and/or their composites. For example, the components of system 10, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polylactide, polyglycolide, polytyrosine carbonate, polycaprolactone and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

The surgical implant system includes a spinal construct 100, which is employed, for example, with an open or mini-open, minimal access and/or minimally invasive including percutaneous surgical technique for implantation at a surgical site within a body of a patient, for example, a section of a spine. In one embodiment, the components of surgical system are configured for fixation with tissue for a surgical treatment to treat various spine pathologies, such as those described herein.

With reference to FIGS. 1-3, in an embodiment, there is provided a spinal construct 100 including a first fastener 110, a second fastener 120 and a connector 140. Fastener 110 includes a first end 112 and a second end 114 configured for penetrating tissue. The first end 112 and second end 114 of first fastener 110 are connected to each other by a shank 116 having an outer surface, which in some embodiments is threaded to allow the fastener to function as a bone screw, for example, a pedicle screw. Second fastener 120 includes a first end 122 and a second end 124 configured for penetrating tissue. The first end 122 and second end 124 of second fastener 120 are connected to each other by a shank 126 having an outer surface, which in some embodiments is threaded to allow the fastener to function as a bone screw, for example, a pedicle screw.

Connector 140 has a first end 150 and a second end 170. The first end 150 of connector 140 includes a first expandable member 152 and the second end 170 includes a second expandable member 172, both configured to receive the first end 112 of fastener 110 or the first end 122 of fastener 120 to fix each fastener to connector 140. The first end 112 of fastener 110 can be rounded and configured to fit within an interior cavity of the first expandable member while allowing rotation and articulation of fastener 110. In some embodiments, shank 116 can have a cylindrical shaft configuration. In various embodiments, securing members 190 and 192 secure connector 140 to the first and second fastener, respectively. In certain embodiments, the first end 150 and second end 170 of connector 150 is joined by a bridge 160 disposed between the two connector ends. Bridge 160, in some embodiments, comprises an adjustable length between first end 150 and second end 170 of connector 140. It is contemplated that the respective cross-sectional geometry of bridge 160 may have various configurations, for example, round, oval, rectangular, irregular, consistent, variable, uniform and non-uniform. Bridge 160 can have various cross-sectional area, geometry, material or material property such as strength, modulus or flexibility. In some embodiments, connector 140 can be monolithic and the connector including first end 150 and second end 170 can be one piece.

With further reference to FIG. 1, in various embodiments, bridge 160 of connector 140 comprises an axis A-A which is perpendicular to the longitudinal axes $L_1$ and $L_2$ of the first and second fastener, respectively.

In some embodiments, each securing member can be a set screw. The spinal construct 100 may be part of a larger orthopedic system comprising a plurality of longitudinal members (e.g., rods, plates, etc.), a plurality of bone fasteners, and/or a plurality of connectors. In some embodiments, the spinal construct 100 is particularly suited for use in the spinal column. It will be understood that various types of connectors (e.g., clamps) can be used in combination with the spinal construct 100.

Shank 116 of fastener 110 defines a longitudinal axis $L_1$ and is configured for fixation to spinal vertebrae. Shank 126 of fastener 120 defines a longitudinal axis $L_2$ and is configured for fixation to spinal vertebrae. It is contemplated that fastener 110 and/or fastener 120 may include alternate bone fixation elements, such as, for example, a nail configuration, barbs, and/or expanding elements.

It is contemplated that fastener 110 can be variously dimensioned, for example, with regard to length, width, diameter and thickness. It is further contemplated that the respective cross-sectional geometry of fastener 110 may have various configurations, for example, round, oval, rectangular, irregular, consistent, variable, uniform and non-uniform. Fastener 110 may have a different cross-sectional area, geometry, material or material property such as strength, modulus or flexibility relative to shank 116.

In some embodiments, as illustrated in FIGS. 1-3, as a result of this application, spinal construct 100 can have a low profile of from about 4 mm to about 5 mm, lower than a majority of other spinal constructs utilizing multiple axial pedicle screws. In use, the medical practitioner, places fasteners 110 and 120 in a location appropriate for treating a spinal disorder. Subsequently, the surgeon can snap on the single level construct 100 onto fasteners 110 and 120 and tightened connector 140 with securing members 190 and 192, for example set screws. FIG. 2 illustrates the securing members 190 and 192 engaging connector 140, which engages fasteners 110 and 120. Securing members 190 and 192 (e.g., set screws) can be turned so that connector 140 can pop or snap onto fasteners 110 and 120. The securing members can be removed from connector 140 by a hand tool or by hand, for example, by rotating the security members in a reverse direction. A tightened spinal construct 100 that has a low profile is illustrated in FIG. 3.

Figure 4:
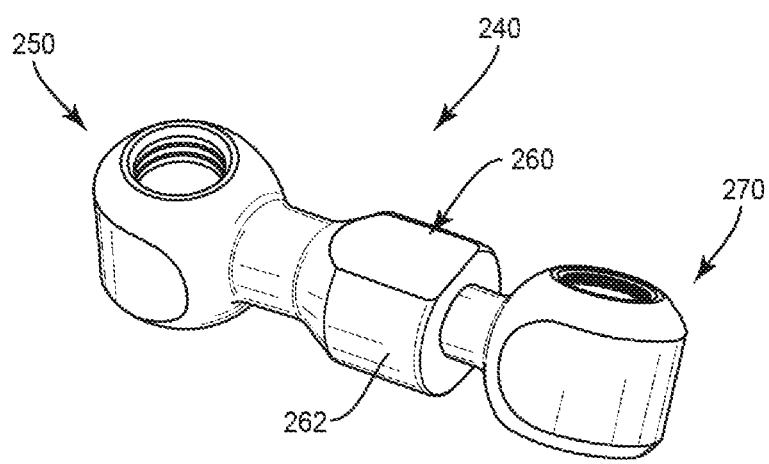
FIG. 4 is a perspective view of components of one embodiment of a surgical implant system in accordance with the principles of the present disclosure.

With reference to FIG. 4, in various embodiments, bridge 260 of connector 240 comprises a coupling member 262, for example, a set screw, fixedly attached to the first end 250 of connector 240. At an end opposite first end of connector 240, coupling member 262 is configured to receive second end 270 of connector 240. Second end 270 of connector 240 can have various configurations. For example, second end 270 can be threaded to function as a screw so as to rotate freely within coupling member 262. In other embodiments, second end 270 of connector 240 can be configured to engage slidably the first end 250 of connector 240. Each end of connector 240 comprises an expandable member (not shown in FIG. 4) at one end configured to engage the first end of a bone screw or fastener. Each end of connector 240 defines a hole configured to receive a securing member, such as a set screw, and the hole can also receive the head of the fastener (e.g., bone screw), in some embodiments, the head is disposed opposite the securing member. For example, first end 250 of connector 240 defines hole 252 and second end 270 of connector 240 defines hole 272. In use, second end 270 can rotate around the latitudinal axis of connector 240 and upon tightening, can also be used to prevent rotation once connector 240 is positioned in a desired location at a desired configuration.

It will be understood that bridge 260 can adjust to different lengths to extend or contract to the size of a vertebra. In some embodiments, the bridge of the connector can selectively extend to the desired length. In some embodiments, the coupling member 262 can extend or contract by a friction fitting between the bridge and the expandable members.

Figure 5:
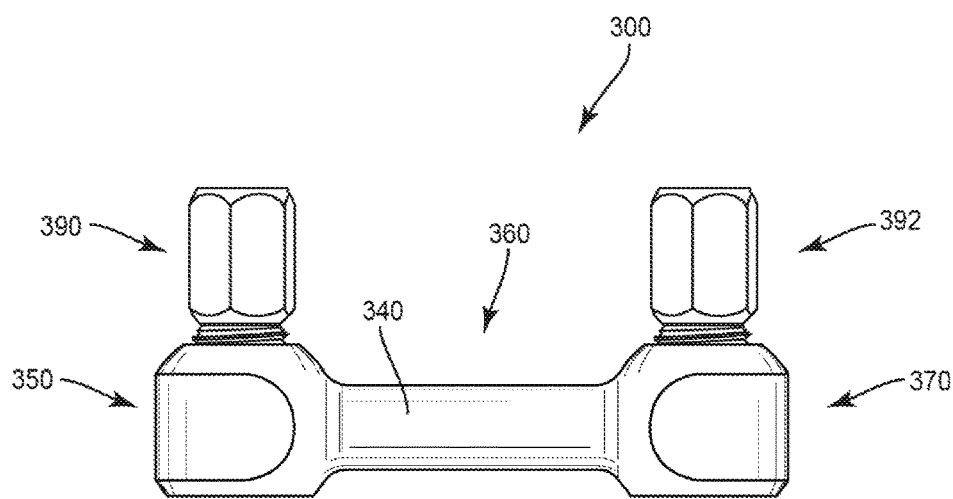
FIG. 5 is a perspective view of components of one embodiment of a surgical implant system in accordance with the principles of the present disclosure.
Figure 6:
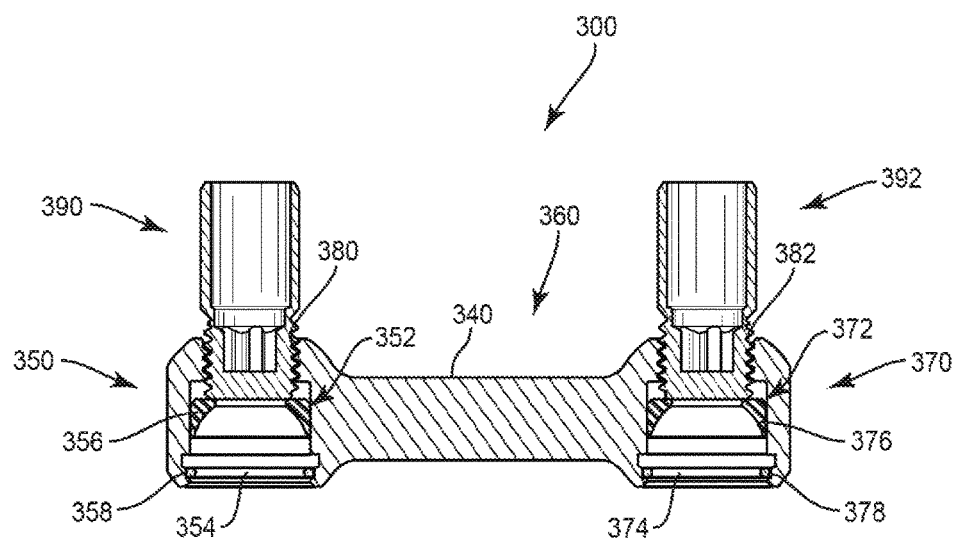
FIG. 6 is a cross-section of the components shown in FIG. 5.

In various embodiments, with reference to FIGS. 5-6, spinal construct 300 comprises a first expandable member 352 disposed in the first end 350 of connector 340. A second expandable member 372 is disposed in the second end 370 of connector 340. Each expandable member can comprise an expansion chamber having two ends; at one end, the expandable member comprises a retaining member 356, 376 and an inner locking ring, 354 and 374 and at the other end, the expandable member defines a hole 380, 382 to receive a securing member 390, 392. Retaining members 356 and 376 can be expandable and are configured to receive the first end of the first fastener and/or the first end of the second fastener (not shown). Each retaining member 356, 376 of expandable members 352, 372 can have various forms comprising a triangle, trapezoid, hexagon, circle, semi-circle, ellipse, rectangle, square or crown shaped adapted for receiving a similarly shaped first end of first and/or second fastener. At the end opposite from the end configured to receive a fastener, expandable t embers 352, 372 define holes 380, 382 configured to receive securing members 390, 392 for attaching the connector 340 onto bone screws or fasteners. In some embodiments, securing members 390 and 392 can be set screws.

With further reference to FIG. 6, each expandable member 352, 372 also comprise a notch 358, 378 configured for receiving an inner locking ring therein. These expandable members are at opposite ends of bridge 360. Each inner locking ring, 354 and 374 can be expandable. In various embodiments, inner locking rings 354, 374 can be made of silicone having a hardness from about 40 durameter to about 80 durameter. In use, when retaining members 356 and 376 contact the first end of a fastener (not shown), they expand radially and then collapse back to their original form thereby being able to engage the first end of a fastener into a tight grip. Once, the first end of a fastener has been received by the retaining member at the end of the connector, the inner locking ring is pushed into the notch of the expandable member to provide a tight fit with the fastener. It will be understood that other mechanisms can be used including friction fit or locking assemblies to lock the connector on the head of the fastener.

First end 350 and second end 370 of connector 340 can have many different shapes, for example spherical, truncated spherical, cylindrical and the like. In certain embodiments, end 350 and end 370 can be substantially C-shaped, having an upper leg, a lower leg including a foot portion extending from one end thereof, and an intermediate portion joining upper and lower legs opposite of foot portion. Each end 350 and/or 370 can define a mouth between the upper leg and the foot portion that is opposite intermediate portion of the C-shaped end. The mouth opens into upper passage portion extending through first end 350 and/or second end 370, with upper passage portion extending in an orthogonal relationship to the longitudinal axis of a fastener. Upper leg has a threaded aperture into which an engaging member, for example a set screw can be threadingly engaged.

In assembly, operation and use, the surgical implant system including spinal construct 100 or 300 is employed with a surgical procedure for treatment of a spinal disorder affecting a section of a spine of a patient, as discussed herein. The spinal construct 100 or 300 may also be employed with other surgical procedures. It is contemplated that the surgical implant system including spinal construct 100 or 300 is attached to spinal vertebrae for fusion and/or dynamic stabilization applications of the affected section of the spine to facilitate healing and therapeutic treatment, while providing flexion, extension and/or torsion capabilities.

In use, to treat the affected section of the spine, a medical practitioner obtains access to a surgical site including spinal vertebrae in any appropriate manner, such as through incision and retraction of tissues. It is envisioned that the surgical implant system including spinal construct 100 or 300 may be used in any existing surgical method or technique including open surgery, mini-open surgery, minimally invasive surgery and percutaneous surgical implantation, whereby spinal vertebrae are accessed through a micro-incision or sleeve that provides a protected passageway to the area. Once access to the surgical site is obtained, the particular surgical procedure is performed for treating the spinal disorder. The surgical implant system including spinal construct 100 or 300 is then employed to augment the surgical treatment. The surgical implant system including spinal construct 100 or 300 can be delivered or implanted as a pre-assembled device or can be assembled in situ. The surgical implant system may be completely or partially revised, removed or replaced, for example, replacing the connector and/or one or all of the components of spinal construct 100 or 300.

Spinal construct 100 or 300 may be employed with a bone screw, pedicle screw or multi-axial screw used in spinal surgery. It is contemplated that spinal construct 100 or 300 may be coated with an osteoconductive material such as hydroxyapatite and/or osteoinductive agent such as a bone morphogenetic protein for enhanced bony fixation. Spinal construct 100 or 300 can be made of radiolucent materials such as polymers. Radiomarkers may be included for identification under x-ray, fluoroscopy, CT or other imaging techniques. Metallic or ceramic radiomarkers, such as tantalum beads, tantalum pins, titanium pins, titanium endcaps and platinum wires can be used, such as being disposed at the end portions of vertebral rod.

It is envisioned that the spinal construct 100 or 300 may be employed with a vertebral rod or connector(s) having an arcuate configuration and an increased length providing the ability to extend over two or more intervertebral elements. It is contemplated that the configuration of the surgical implant system may provide load sharing, dynamic and/or flexible stabilization over a plurality of intervertebral levels, including treated and untreated vertebral and intervertebral levels.

In one embodiment, the spinal construct includes an agent, which includes a bone growth promoting material, which may be disposed, packed or layered within, on or about the components and/or surfaces thereof. The bone growth promoting material, such as, for example, bone graft can be a particulate material, which may include an osteoconductive material such as hydroxyapatite and/or an osteoinductive agent such as a bone morphogenic protein (BMP) to enhance bony fixation of spinal construct 100 or 300 with the adjacent vertebrae.

In other embodiments, a method for treating a spinal disorder is provided. The method includes implanting a spinal construct comprising a first fastener, a second fastener and a connector. The connector utilized in this method has two ends, a first end including and first expandable member and a second end including a second expandable member. Each expandable member of the connector is engageable with and can be snapped onto the first end of each fastener. After the spinal construct is implanted, the method includes securing the first end of the connector to the first fastener with a first securing member and securing the second end of the connector to the second fastener with a second securing member. In various embodiments, the method provided herein is for treating a spinal disorder, wherein the spinal construct conforms to the curvature of the spine.

In some embodiments, the at least two bone screws are implanted into at least one or more vertebrae and the connector is attached to the heads of each bone screw so that the connector pops or snaps on the head of the bone screw. In this way, the connector can easily be applied to the bone screw.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
a connector extending along a longitudinal axis between a first end and a second end, the first end comprising a passageway, a shaft of the second end being positioned within the passageway such that the second end can translate relative to the first end along the longitudinal axis, the ends each comprising a threaded hole extending through a top surface of the connector,
wherein the first end comprises a first expandable member including an inner surface defining a cavity configured to receive a head of a first bone fastener and the second end comprises a second expandable member including an inner surface defining a cavity configured to receive a head of a second bone fastener, the cavities each including an opening extending through a bottom surface of the connector, the expandable members each comprising a retaining member positioned in a respective one of the cavities, an inner locking ring positioned in a respective one of the cavities and a notch that extends into a respective one of the inner surfaces, the openings each having a maximum diameter greater than a maximum diameter of each of the retaining members, the retaining members being configured to expand radially and then collapse back to their original form when one of the heads contacts one of the retaining members, the inner locking rings being configured to be pushed into one of the notches when one of the heads is received by one of the retaining members.

2. A spinal construct as recited in claim 1, wherein the second end is rotatable relative to the first end about the longitudinal axis.

3. A spinal construct as recited in claim 1, wherein the threaded holes are each configured to engage a set screw, the holes each extending transverse to the longitudinal axis.

4. A spinal construct as recited in claim 1, further comprising a first set screw positioned in the threaded hole in the first end and a second set screw positioned in the threaded hole in the second end.

5. A spinal construct as recited in claim 1, further comprising a first bone screw positioned in the first end and a second bone screw positioned in the second end.

6. A spinal construct as recited in claim 1, wherein the inner locking rings are expandable and are made of silicone having a hardness from about 40 durometer to about 80 durometer.

7. A spinal construct as recited in claim 1, wherein the shaft is slidably disposed within the passageway.

8. A spinal construct as recited in claim 1, wherein the second end is threaded to function as a screw so as to rotate freely within the passageway.

9. A spinal construct as recited in claim 1, wherein the inner surfaces each extend perpendicular to the longitudinal axis, the retaining members each comprising a wall that engages a respective one of the inner surfaces, the walls each extending perpendicular to the longitudinal axis.

10. A spinal construct comprising:
a connector extending along a longitudinal axis between a first end and a second end, the first end comprising a passageway, a shaft of the second end being positioned within the passageway such that the second end can translate relative to the first end in opposite directions along the longitudinal axis;
a first bone screw coupled to the first end;
a second bone screw coupled to the second end;
a first set screw positioned in a threaded hole in the first end; and
a second set screw positioned in a threaded hole in the second end, the threaded holes extending through a top surface of the connector,
wherein the first end comprises a first expandable member including an inner surface defining a cavity configured to receive a head of the first bone screw and the second end comprises a second expandable member including an inner surface defining a cavity configured to receive a head of the second bone screw, the cavities each including an opening extending through a bottom surface of the connector, the expandable members each comprising a retaining member positioned in a respective one of the cavities, an inner locking ring positioned in a respective one of the cavities and a notch that extends into a respective one of the inner surfaces, the openings each having a maximum diameter greater than a maximum diameter of each of the retaining members, the retaining members being configured to expand radially upon direct engagement with one of the heads and then collapse back to their original form, the inner locking rings each being configured to be pushed into one of the notches when one of the heads is received by one of the retaining members.

11. A spinal construct as recited in claim 10, wherein the second end is rotatable relative to the first end about the longitudinal axis.

12. A spinal construct as recited in claim 10, wherein the shaft is slidably disposed within the passageway.

13. A spinal construct as recited in claim 10, wherein the second end is threaded to function as a screw so as to rotate freely within the passageway.

14. A spinal construct as recited in claim 10, wherein the holes each extend transverse to the longitudinal axis.

15. A spinal construct as recited in claim 10, wherein the shaft is cylindrical.

16. A spinal construct comprising:
  a connector extending along a longitudinal axis between a first end and a second end, the first end comprising a passageway, a shaft of the second end being positioned within the passageway such that the second end can translate relative to the first end in opposite directions along the longitudinal axis, the ends each comprising an expandable member and a threaded hole configured to engage a set screw, the threaded holes extending through a top surface of the connector;
  a first bone screw coupled to the expandable member of the first end; and
  a second bone screw coupled to the expandable member of the second end,
  wherein the expandable members each comprise an inner surface defining a cavity, a retaining member positioned in the cavity, an inner locking ring positioned in the cavity and a notch that extends into the inner surface, the retaining member being positioned between the inner locking ring and a respective one of the threaded holes, the cavities each including an opening extending through a bottom surface of the connector, the openings each having a maximum diameter greater than a maximum diameter of each of the retaining members, the retaining members being configured to expand radially and then collapse back to their original form when one of the screws contacts one of the retaining members, the inner locking rings each being configured to be pushed into one of the notches when one of the screws is received by one of the retaining members.

17. A spinal construct as recited in claim 16, wherein the second end is rotatable relative to the first end about the longitudinal axis.

18. A spinal construct as recited in claim 16, wherein the shaft is slidably disposed within the passageway.

19. A spinal construct as recited in claim 16, wherein the second end is threaded to function as a screw so as to rotate freely within the passageway.

20. A spinal construct as recited in claim 16, wherein the shaft is cylindrical.

\* \* \* \* \*

UNITED STATES PATENT AND TRADEMARK OFFICE
CERTIFICATE OF CORRECTION

PATENT NO. : 10,188,427 B2
APPLICATION NO. : 15/499447
DATED : January 29, 2019
INVENTOR(S) : Rezach et al.

It is certified that error appears in the above-identified patent and that said Letters Patent is hereby corrected as shown below:

On the Title Page

In Item (73), under "Assignee", in Column 1, Line 1, delete "Orthopeic," and insert -- Orthopedic, --, therefor.

In Item (62), under "Related U.S. Application Data", in Column 1, Line 2, delete "2015." and insert -- 2015, now abandoned. --, therefor.

In the Specification

In Column 1, Line 6, delete "of application" and insert -- of --, therefor.

In Column 1, Line 7, delete "2015," and insert -- 2015, now abandoned. --, therefor.

In Column 1, Line 64, delete "and first" and insert -- a first --, therefor.

In Column 2, Line 21, delete "disclosure; and" and insert -- disclosure; --, therefor.

In Column 2, Line 24, delete "disclosure." and insert -- disclosure; and --, therefor.

In Column 2, Line 40, delete "receivers minimizing inventor" and insert -- receivers thereby minimizing inventory --, therefor.

In Column 6, Line 8, delete "white" and insert -- while --, therefor.

In Column 6, Line 14, delete "connector 150" and insert -- connector 140 --, therefor.

In Column 7, Line 55, delete "t embers" and insert -- members --, therefor.

In Column 9, Line 28, delete "and first" and insert -- a first --, therefor.

Signed and Sealed this
Second Day of July, 2019

Andrei Iancu
*Director of the United States Patent and Trademark Office*